US00PP11931P2

(12) United States Plant Patent
Kientzler

(10) Patent No.: US PP11,931 P2
(45) Date of Patent: Jun. 19, 2001

(54) NEW GUINEA IMPATIENS PLANT NAMED 'KIZIZ'

(75) Inventor: Ludwig Kientzler, Gensingen (DE)

(73) Assignee: Paul Ecke Ranch, En Cinitas, CA (US)

( * ) Notice: Subject to any disclaimer, the term of this patent is extended or adjusted under 35 U.S.C. 154(b) by 0 days.

(21) Appl. No.: 09/439,354

(22) Filed: Nov. 15, 1999

(51) Int. Cl.[7] ..... A01H 5/00
(52) U.S. Cl. ..... Plt./318
(58) Field of Search ..... Plt./318

(56) References Cited

PUBLICATIONS

GTITM UPOVROM Citation for 'Kiziz' as per CA PBR 99–1713; Jun. 15, 1999.*

* cited by examiner

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of New Guinea Impatiens plant named 'Kiziz', characterized by its large light and dark orange bi-colored flowers; upright and very compact growth habit; and very dark green leaves tinged with anthocyanin.

1 Drawing Sheet

BACKGROUND OF THE INVENTION

The present invention relates to a new and distinct cultivar of New Guinea Impatiens plant, botanically known as *Impatiens hawkeri,* and hereinafter referred to by the cultivar name 'Kiziz'.

The new cultivar is a product of a planned breeding program conducted by the Inventor in Gensingen, Germany. The objective of the breeding program was to develop early-flowering varieties with numerous flowers, freely-branching and uniform plant habit, attractive flower and foliage colors, and good flower form.

The new cultivar originated from a cross made by the Inventor of the proprietary selection identified as G26 as the male, or pollen parent, with the proprietary selection identified as A330 as the female, or seed parent.

The cultivar 'Kiziz' was discovered and selected by the Inventor as a flowering plant within the progeny of the stated cross in a controlled environment in Gensingen, Germany, in April, 1997.

Asexual reproduction of the new cultivar by terminal cuttings taken at Gensingen, Germany, has shown that the unique features of this new cultivar are stable and reproduced true to type in successive generations of asexual reproduction.

SUMMARY OF THE INVENTION

The following traits have been repeatedly observed and are determined to be the unique characteristics of 'Kiziz'. These characteristics in combination distinguish 'Kiziz' as a new and distinct cultivar:

1. Large light and dark orange bi-colored flowers.
2. Upright and very compact growth habit.
3. Very dark green leaves tinged with anthocyanin.

Plants of the new cultivar can be compared to plants of the commercial cultivar 'Lycia', disclosed in U.S. Plant Pat. No. 10,322. However, in side-by-side comparisons conducted in Encinitas, Calif., plants of the new cultivar differ from plants of the cultivar 'Lycia' in the following characteristics:

1. Plants of the new cultivar are more compact than plants of the cultivar 'Lycia'.

2. Plants of the new cultivar have smaller leaves than plants of the cultivar 'Lycia'.

3. Flowers of plants of the new cultivar are smaller but more round than flowers of plants of the cultivar 'Lycia'.

4. Flower color of plants of the new cultivar is light and dark orange whereas flower color of plants of the cultivar 'Lycia' is light pink and orange.

5. Plants of the new cultivar flower about one week earlier than plants of the cultivar 'Lycia'.

A detailed comparison of plants of the cultivars 'Kiziz' and 'Lycia' appears in Chart A at the end of the specification.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical plant of the cultivar 'Kiziz'.

The photograph at the bottom of the sheet comprises a comparison close-up view of typical flower buds, flowers and upper and lower surfaces of leaves of the cultivars 'Kiziz' (left) and 'Lycia' (right). Flower and foliage colors in the photographs may differ from the actual colors due to light reflectance.

DETAILED BOTANICAL DESCRIPTION

Plants of the cultivar 'Kiziz' have not been observed under all possible environmental conditions. The phenotype may vary somewhat with variations in environment such as temperature and light intensity, without, however, any variance in genotype. The following observations, measurements and comparisons describe plants grown in 25-cm hanging baskets in Encinitas, Calif., under commercial practice in a polyethylene-covered greenhouse with day temperatures averaging 23° C., night temperatures averaging 19° C., and light levels about 3,000 foot-candles. Plants were about 17 weeks old after planting a rooted cutting.

In the following description, color references are made to The Royal Horticultural Society Colour Chart except where general terms of ordinary dictionary significance are used.

Classification:

*Botanical.*—*Impatiens hawkeri* cultivar 'Kiziz'.

*Commercial.*—New Guinea Impatiens cultivar 'Kiziz'.

Parentage:

*Male parent.*—Proprietary selection of *Impatiens hawkeri* identified as G26.

*Female parent.*—Proprietary selection of *Impatiens hawkeri* identified as A330.

Propagation:

*Type cutting.*—Terminal cuttings.

*Time to initiate roots.*—About 10 days with 20° C. soil temperature.

*Time to develop roots.*—About 21 days with 20° C. soil temperature.

*Root description.*—Fine and fibrous.

Plant description:

*Plant form.*—Upright and V-shaped; very compact; rounded canopy.

*Growth habit.*—Low to moderately vigorous. Appropriate for 10 to 20-cm containers.

*Crop time.*—For finished flowering plants grown in a 10-cm container, about 8 to 10 weeks from rooted cuttings are required; for finished flowering plants grown in a 25-cm container, about 17 weeks from rooted cuttings are required.

*Plant size.*—Height: About 14 cm. Width or spread: About 19.5 cm.

*Lateral branches.*—Quantity: About 6. Length: About 11 cm. Diameter: About 8 mm. Internode length: About 1.9 cm. Color: 181B.

*Foliage description.*—Leaves simple, generally symmetrical, abundant, opposite or in whorls, horizontal to plant. Mostly flat. Length: About 8.25 cm. Width: About 3.9 cm. Shape: Elliptic. Apex: Acuminate. Base: Attenuate. Margin: Entire with ciliation. Texture: Mostly smooth; glossy. Color: Young foliage, upper surface: Darker than 147A. Young foliage, lower surface: 59A. Fully expanded foliage, upper surface: Darker than 147A tinged with anthocyanin, close to 59A. Fully expanded foliage, lower surface: 59A. Venation, upper surface: 59B. Venation, lower surface: 59A. Petiole: Length: About 1.8 cm. Diameter: About 4 mm. Color: 60B.

Flower description:

*Flower type and habit.*—Light and dark orange bi-colored flowers. Freely and continuously flowering. Flowers arise from leaf axils. Usually about 6 flowers and flower buds per lateral branch. Flowers positoned above the foliage and face upward and outward. Flowers rounded rectangular. Flowers persistent.

*Flowering season.*—Year-round under greenhouse conditions. In the garden, flowering is continuous from spring until fall.

*Flower size.*—Length: About 6 cm. Width: About 5.8 cm. Depth: About 1.5 cm.

*Flower buds.*—Length: About 1.6 cm. Diameter: About 1 cm. Shape: Ovoid. Color: 43B.

*Petals.*—Quantity: Five. Length: Upper petal: About 2.8 cm. Middle petals: About 2 cm. Lower petals: About 3.2 cm. Width: Upper petal: About 4 cm. Middle petals: About 2.2 cm. Lower petals: About 3 cm. Shape: Cordate. Apex: Cordate. Base: Acute. Margin: Entire. Texture: Velvety, smooth. Color: When opening, upper surface: Upper petal, brighter than 32A; middle and lower petals, 41C. When opening, lower surface: 50D. Fully opened, upper surface: Upper petal, mostly 33A (center) and 49B towards lateral margins; middle and lower petals, background 49B, with central lines and towards base 33A, and base, 57A; color fading to 33B (background) and 49C (central areas/lines and towards base) with subsequent development. Fully opened, lower surface: 40C to 40D.

*Spur.*—Length: About 5.5 cm. Shape: Narrow and curved. Color: 2D tinged with 36A.

*Peduncles.*—Length: About 4.8 cm. Angle: Greater than 45° from vertical. Strength: Strong. Color: 145C.

*Reproductive organs.*—Androecium: Stamen number: Five, anthers fused, filaments free. Anther shape: Obovate. Anther size: 3 mm by 5 mm. Anther color: 10B. Amount of pollen: Moderate. Pollen color: 10D. Gynoecium: Five-loculate fused. Pistil number: One. Pistil length: About 4 mm. Stigma color: 60A. Ovary color: 144A.

Disease resistance: Under commercial conditions, resistance to pathogens common to New Guinea Impatiens has not been observed.

Seed development: Seed production has not been observed.

CHART A

| CHARACTERISTIC | 'KIZIZ' | 'LYCIA' |
|---|---|---|
| PLANT HEIGHT | About 14 cm | About 20 cm |
| PLANT WIDTH | About 19.5 cm | About 26 cm |
| VIGOR | Low to moderate | Moderate |
| LEAF LENGTH | About 8.25 cm | About 10 cm |
| LEAF WIDTH | About 3.9 cm | About 5 cm |
| PETIOLE LENGTH | About 1.8 cm | About 3 cm |
| FLOWER DIAMETER | About 6 by 5.8 cm | About 7.5 by 6.5 cm |
| PETAL COLOR, MATURE, UPPER SURFACE | Upper petal, mostly 33A (center), 49B towards lateral margins; middle and lower petals, background 49B, central lines and towards base 33A, base 57A | Upper petal, mostly 40A (center), 50D towards lateral margins; middle and lower petals, background 50D, central lines 40A to 40B, base 57B |
| PETAL COLOR, MATURE, LOWER SURFACE | 40C to 40D | 41B to 50D towards margins |
| PETAL COLOR, FADING TO | Background, 33B; central areas/lines and towards base, 49C | Background, 56B; central areas/lines, 40C to 40D |
| SPUR LENGTH | About 5.5 cm | About 4.5 cm |
| SPUR COLOR | 2D tinged with 36A | Base, 59A; apex, 144A |
| PEDUNCLE LENGTH | About 4.8 cm | About 2.8 cm |
| PEDUNCLE COLOR | 145C | 149B |

It is claimed:

1. A new and distinct cultivar of New Guinea Impatiens plant named 'Kiziz', as illustrated and described.

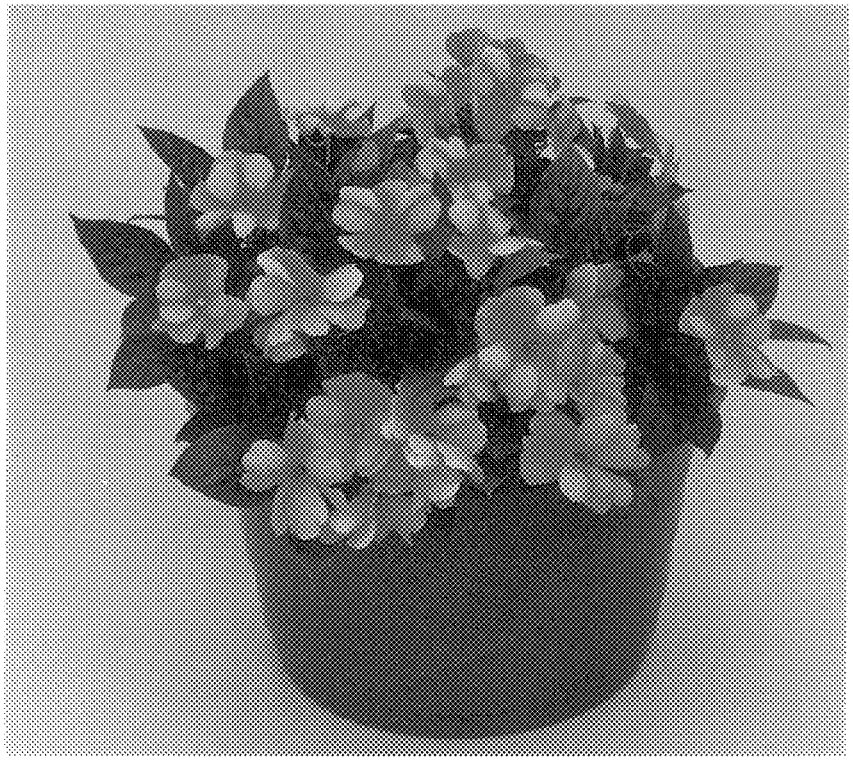
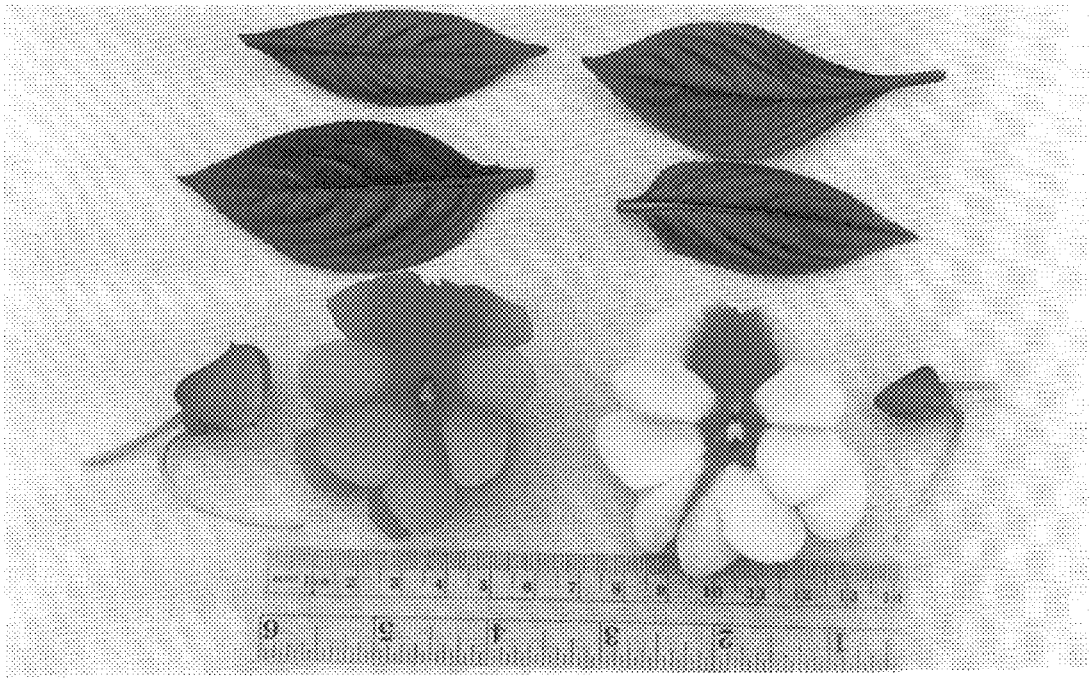

* * * * *